United States Patent [19]

Funaki et al.

[11] Patent Number: 4,985,570

[45] Date of Patent: Jan. 15, 1991

[54] PRODUCTION OF TETRAHYDROPHTHALIMIDE COMPOUND

[75] Inventors: Yuji Funaki, Toyonaka; Masayuki Fukushima, Minoo, both of Japan

[73] Assignee: Sumitomo Chemical Company, Limited, Osaka, Japan

[21] Appl. No.: 239,470

[22] Filed: Sep. 1, 1988

[30] Foreign Application Priority Data

Sep. 1, 1987 [JP] Japan .................................. 62-218608
Apr. 27, 1988 [JP] Japan .................................. 63-107008

[51] Int. Cl.$^5$ .......................................... C07D 209/48
[52] U.S. Cl. ...................................................... 548/513
[58] Field of Search ............................................ 548/513

[56] References Cited

U.S. PATENT DOCUMENTS

| 4,500,719 | 3/1985 | Oba ........................................ 548/522 |
| 4,670,046 | 6/1987 | Nagano et al. .......................... 71/96 |

FOREIGN PATENT DOCUMENTS

| 049508A1 | 10/1981 | European Pat. Off. . |
| 0049508 | 4/1982 | European Pat. Off. . |
| 0061741 | 10/1982 | European Pat. Off. . |
| 0083055 | 7/1983 | European Pat. Off. . |
| 0150064 | 7/1985 | European Pat. Off. . |
| 1346792 | 1/1971 | United Kingdom . |

OTHER PUBLICATIONS

Chem. Abs. 101:165569j, p. 232.

*Primary Examiner*—Robert A. Wax
*Assistant Examiner*—F. Tsung
*Attorney, Agent, or Firm*—Birch, Stewart, Kolasch & Birch

[57] ABSTRACT

A process for preparing a compound of the formula:

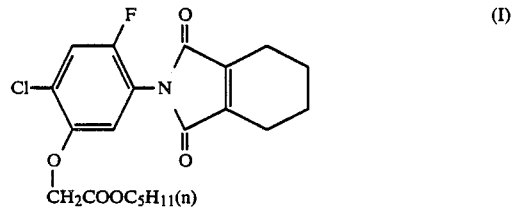

(I)

in an excellent yield with high purity, which comprises reacting a compound of the formula:

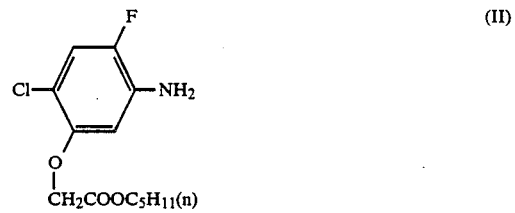

(II)

with 3,4,5,6-tetrahydrophthalic anhydride in the presence of a catalyst system consisting of a nitrogen-containing base and a lower fatty acid.

13 Claims, No Drawings distilled off under reduced pressure to give 4-chloro-2-fluoro-5-(pentyloxycarbonylmethyloxy)aniline (Compound (II)) (90 g). Yield, 75%. b.p., 145°–149° C./0.4 mmHg. m.p., 32°–34° C.

NMR δ (CDCl$_3$, TMS) (ppm): 7.00 (1H, d, J=10 Hz), 6.37 (1H, d, J=7 Hz), 4.60 (2H, s), 4.20 (2H, t, J=6 Hz), 3.75 (2H, brs), 1.10–1.90 (6H, m), 0.92 (3H, t, J=6 Hz).

EXAMPLE 3

Preparation of the compound (II):

Hydrogen gas (1.3 liters) was introduced into a mixture of the compound (III) (6.4 g), 5% palladium-carbon (0.32 g) and toluene (64 g) at room temperature while stirring in 1 hour. After removal of the catalyst from the reaction mixture, the solvent was removed under reduced pressure, and the residue was purified by silica gel column chromatography to give 4-chloro-2-fluoro-5-(pentyloxycarbonylmethyloxy)aniline (3.6 g). Yield, 62%.

EXAMPLE 4

Preparation of the compound (I):

A mixture of the compound (II) (12.0 g), 3,4,5,6-tetrahydrophthalic anhydride (7.56 g), piperidine (0.18 g), propionic acid (0.30 g) and toluene (24 g) was heated under reflux for 5 hours, during which water as by-produced was azeotropically removed. To the reaction mixture, toluene (24 g) and water (24 g) were added, and the organic layer was separated and concentrated under reduced pressure. To the residue, water (18 g) and methanol (33 g) were added, and the precipitated crystals were collected by filtration to give N-[4-chloro-2-fluoro-5-(pentyloxycarbonylmethyloxy)-phenyl]-3,4,5,6-tetrahydrophthalimide (Compound (I)) (16.1 g). By the use of a high speed liquid chromatography, the purity of the compound (I) as the major product and the amount of the by-produced 4-chloro-2-fluoro-5-(pentyloxycarbonylmethyloxy)acetanilide (hereinafter referred to as "N-acetyl compound") as a contaminant were determined according to the inner standard method and the area comparison method, respectively.

Yield, 92.0%.

Purity: 92.3% (N-acetyl compound content, less than 0.1%).

NMR δ (CDCl$_3$, TMS) (ppm) 7.22 (1H, d, J=10 Hz), 6.75 (1H, d, J=7 Hz), 4.6 (2H, s), 4.1 (2H, t, J=6 Hz), 2.40 (4H, m), 1.80 (4H, m), 1.10 - 1.80 (6H, m), 0.85 (3H, t, J=6 Hz).

IR (Nujol): 1750, 1720 (cm$^{-1}$).

m.p.: 90°–91° C.

EXAMPLE 5

Preparation of the compound (I):

A mixture of the compound (II) (12.0 g), 3,4,5,6-tetrahydrophthalic anhydride (7.56 g), triethylamine (9.42 g), acetic acid (0.75 g) and 1,2-dichloroethane (24 g) was heated under reflux for 8 hours. The reaction mixture was washed with water (24 g). The organic layer was separated and treated as in Example 4 to give the compound (I) (16.2 g).

Yield, 92.5%.

Purity: 94.7% (N-acetyl compound content, 0.1%.

EXAMPLE 6

Preparation of the compound (I):

A mixture of the compound (II) (12.0 g), 3,4,5,6-tetrahydrophthalic anhydride (7.56 g), piperidine (0.36 g), acetic acid (0.5 g) and toluene (24 g) was refluxed at 88° to 92° C. under a pressure of about 300 mmHg for 4 hours, during which water was azeotropically removed. The reaction mixture was then treated as in Example 4 to give the compound (I) (16.7 g).

Yield, 95.2%.

Purity: 97.0% (N-acetyl compound content, less than 0.1%).

COMPARATIVE EXAMPLE 1

To a solution of N-(4-chloro-2-fluoro-5-hydroxyphenyl)-3,4,5,6-tetrahydrophthalimide (3 g) in dimethylformamide (100 ml), anhydrous potassium carbonate (0.8 g) and then amyl chloroacetate (1.9 g) were added, and the resultant mixture was heated at 70° to 80° C. for 3 hours. The reaction mixture was cooled to room temperature, admixed with water and extracted with diethyl ether. The ethereal layer was washed with water, dried over anhydrous magnesium sulfate and concentrated under reduced pressure. The residue was purified by silica gel column chromatography to give the compound (I) (1.8 g).

Yield, 42.0%.

Purity: 98.0%.

COMPARATIVE EXAMPLE 2

A mixture of the compound (II) (12.0 g), 3,4,5,6-tetarhydrophthalic anhydride (7.56 g) and acetic acid (50 g) was heated at 90° to 95° C. for 7 hours. The reaction mixture was cooled to room temperature, and water (75 g) was added thereto. The precipitated crystals were collected by filtration to give the compound (I) (15.7 g).

Yield, 89.3%.

Purity: 88.7% (N-acetyl compound content, 5.1%.

COMPARATIVE EXAMPLE 3

A mixture of the compound (II) (12.0 g), 3,4,5,6-tetarhydrophthalic anhydride (7.56 g) and acetic acid (50 g) was heated under reflux for 2 hours. The reaction mixture was cooled to room temperature, and water (75 g) was added thereto. The precipitated crystals were collected by filtration to give the compound (I) (15.4 g).

Yield, 88.0%.

Purity: 87.0% (N-acetyl compound content, 7.2%.

COMPARATIVE EXAMPLE 4

A mixture of the compound (II) (12.0 g), 3,4,5,6-tetarhydrophthalic anhydride (7.56 g) and toluene (50 g) was heated under reflux for 12 hours. Analysis by high speed liquid chromatography revealed the presence of 20% of the compound (II) as unreacted. The reaction mixture was concentrated under reduced pressure, and the residue was purified by silica gel column chromatography to give the compound (I) (10.9 g).

Yield, 62.0%.

Purity: 98.0%.

COMPARATIVE EXAMPLE 5

A mixture of the compound (II) (12.0 g) and 3,4,5,6-tetarhydrophthalic anhydride (7.56 g) was heated at 85° to 90° C. for 10 hours. Analysis by high speed liquid chromatography revealed the presence of 72% of the compound (I) and 9% of the compound (II) as unreacted together with many other impurities. The reaction mixture was purified by silica gel column chromatography to give the compound (I) (11.4 g).

Yield: 65.0%.
Purity: 98.2%.

COMPARATIVE EXAMPLE 6

A mixture of the compound (II) (12.0 g), 3,4,5,6-tetarhydrophthalic anhydride (7.56 g), triethylamine (0.4 g) and toluene (50 g) was heated under reflux for 10 hours. The reaction mixture was cooled to room temperature and washed with water. The toluene layer was separated and concentrated under reduced pressure. Analysis of the resulting product revealed that it contains the compound (I) in a purity of about 77% and a large amount of a compound of the following formula as the impurity:

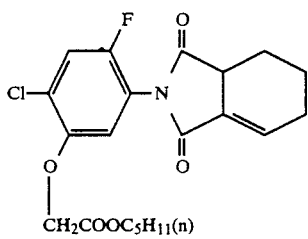

Purification of the above product by silica gel column chromatography gave the compound (I) (13.7 g).

Yield: 77.9%.
Purity: 98.2%.

COMPARATIVE EXAMPLE 7

A mixture of the compound (II) (12.0 g), 3,4,5,6-tetarhydrophthalic anhydride (7.56 g), p-toluenesulfonic acid (0.4 g) and toluene (24 g) was refluxed for 10 hours, during which water was azeotropically removed. The reaction mixture was treated in the same manner as in Example 4 to give the compound (I) (15.6 g).

Yield: 88.9%.
Purity: 80.9%.

Still, the product contained a large amount of a compound of the formula as the impurity:

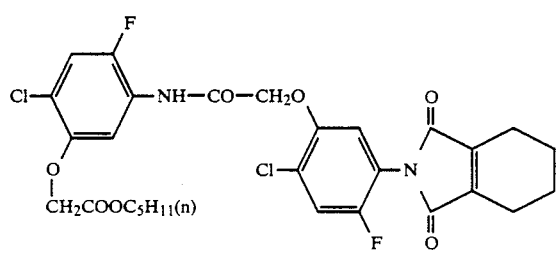

What is claimed is:

1. A process for preparing a compound of the formula:

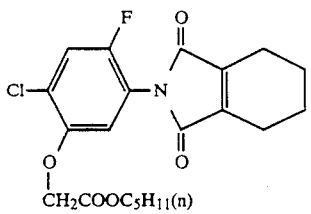

, which comprises reacting a compound of the formula:

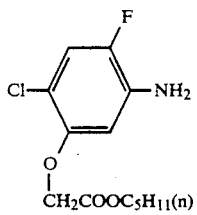

selected from the group consisting of diethylamine, dibutylamine, diethanolamine, triethylamine, tributylamine, triethanolamine, N,N-dimethylaniline, N,N-diethylaniline, pyridine, piperidine, imidazole, morpholine, quinoline, and N,N-diethylaminopyridine;
   with 3,4,5,6-tetrahydrophthalic anhydride in the presence of a catalyst system consisting of a nitrogen-containing base other that said compound (II) and a lower aliphatic acid selected from the group consisting of acetic acid, proprionic acid, and butyric acid.

2. The process according to claim 1, wherein 3,4,5,6-tetrahydrophthalic anhydride is used in an amount of 1.0 to 2.0 equivalents to one equivalent of the compound (II).

3. The process according to claim 1, wherein the nitrogen-containing base and the lower aliphatic acid are used respectively in amounts of 0.01 to 0.5 equivalents to one equivalent of the compound (II) and of 1.0 to 5.0 equivalents to one equivalent of the nitrogen-containing base.

4. The process according to claim 1, wherein said compound (II) is reacted in an organic solvent selected from the group consisting of hydrocarbons, halogenated hydrocarbons and ketones.

5. The process according to claim 4, wherein said organic solvent is a member selected from the group consisting of toluene, xylene, benzene, 1,2-dichloroethane, chlorobenzene, chloroform, carbon tetrachloride and methyl isobutyl ketone.

6. The process according to claim 1, wherein said compound (II) is reacted in a solvent at a temperature of about 50° C. to the boiling temperature of said solvent.

7. The process according to claim 1, wherein said compound (II) is reacted at a temperature of about 80° to 120° C.

8. The process according to claim 1, wherein said compound (II) is reacted for a period of about 1 to 10 hours.

9. The process according to claim 2, wherein 3,4,5,6-tetrahydrophthalic anhydride is used in an amount of 1.0 to 1 3 equivalents to one equivalent of the compound (II).

10. The process according to claim 3, wherein the nitrogen-containing base and the lower aliphatic acid are used respectively in amounts of 0.05 to 0.1 equivalents to one equivalent of the compound (II) and of 1.0 to 2.0 equivalents to one equivalent of the nitrogen-containing base.

11. The process according to claim 9, wherein the nitrogen-containing base and the lower aliphatic acid are used respectively in amounts of 0.05 to 0.1 equivalents to one equivalent of the compound (II) and of 1.0 to 2.0 equivalents to one equivalent of the nitrogen-containing base.

12. The process according to claim 11, wherein said compound (II) is reacted in an organic solvent at a temperature of about 80° to 120° C. for a period of about 1 to 10 hours.

13. The process according to claim 1, wherein said nitrogen-containing base is piperdine or triethylamine, and wherein said lower aliphatic acid is propionic acid or acetic acid.

* * * * *

UNITED STATES PATENT AND TRADEMARK OFFICE
CERTIFICATE OF CORRECTION

PATENT NO. : 4,985,570
DATED : January 15, 1991
INVENTOR(S) : Yuji FUNAKI and Masayuki FUKUSHIMA It is certified that error appears in the above-indentified patent and that said Letters Patent is hereby corrected as shown below:

Column 8, lines 24-34 should be changed to read
--with 3,4,5,6-tetrahydrophthalic anhydride in the
presence of a catalyst system consisting of a
nitrogen-containing base other than said compound (II)
selected from the group consisting of diethylamine,
dibutylamine, diethanolamine, triethylamine,
tributylamine, triethanolamine, N,N-dimethylaniline,
N,N-diethylaniline, pyridine, piperidine, imidazole,
morpholine, quinoline, and N,N-diethylaminopyridine;
and a lower aliphatic acid selected from the group
consisting of acetic acid, proprionic acid, and butyric
acid.--

Signed and Sealed this

Fifteenth Day of August, 1995

Attest:

BRUCE LEHMAN

*Attesting Officer*   *Commissioner of Patents and Trademarks*